US005756750A

United States Patent [19]
Cao et al.

[11] Patent Number: 5,756,750
[45] Date of Patent: May 26, 1998

[54] CONTINUOUS PROCESSES FOR THE HYDROLYSIS OF CYANOPYRIDINES UNDER SUBSTANTIALLY ADIABATIC CONDITIONS

[75] Inventors: Wei Cao; Robert A. Kattau, both of Indianapolis; George Kreilis, Zionsville, all of Ind.

[73] Assignee: Reilly Industries, Inc., Indianapolis, Ind.

[21] Appl. No.: 798,313

[22] Filed: Feb. 7, 1997

Related U.S. Application Data

[60] Provisional application No. 60/011,424, Feb. 9, 1996.

[51] Int. Cl.$^6$ .................. C07D 213/80; C07D 213/56
[52] U.S. Cl. ..................... 546/319; 546/317; 546/286
[58] Field of Search ......................... 546/286, 317, 546/319

[56] References Cited

U.S. PATENT DOCUMENTS

| | | | |
|---|---|---|---|
| 2,471,518 | 5/1949 | Duesel | 546/317 |
| 4,314,064 | 2/1982 | Beschke et al. | 546/317 |
| 4,959,478 | 9/1990 | Moller | 546/319 |
| 5,395,758 | 3/1995 | Takashima et al. | 435/122 |

FOREIGN PATENT DOCUMENTS

| | | | |
|---|---|---|---|
| 93007000CA | 1/1993 | Japan . | |
| 7706612-A | of 0000 | Netherlands . | |
| 1288183A1 | 2/1987 | U.S.S.R. | C07D 213/79 |
| 1553530A1 | 3/1990 | U.S.S.R. | C07D 213/81 |
| 1553531 | 3/1990 | U.S.S.R. . | |
| 1553531A1 | 3/1990 | U.S.S.R. | C07D 213/81 |

OTHER PUBLICATIONS

Krewson, C.F. and Couch, J.F., "The Hydrolysis of Nicotinonitrile by Ammonia", *J. Am. Chem. Soc.*, vol. 65, pp. 2256–7 (1943).

Suvorov, B.V., Kagarlitskii, A.D., Suslova, N.V., Efremov, Yu. G. and Erzhanov, M.K., "Continuous Method For Hydrolysis of 3–Cyanopyridine to Nicotinamide and Nicotinic Acid", *J. App. Chem. of the USSR*, (English Translation: 45:2716–2718(1972)).

*Primary Examiner*—C. Warren Ivy
*Assistant Examiner*—Charanuit S. Aulakh
*Attorney, Agent, or Firm*—Woodard, Emhardt, Naughton, Moriarty & McNett, Patent and Trademark Attorneys

[57] ABSTRACT

Described are preferred processes for hydrolyzing substituted and unsubstituted cyanopyridines in the presence of a base and under substantially adiabatic conditions to produce pyridine substituted amides and/or pyridine substituted carboxylic acids. Preferred processes can be conducted in a variety of continuous reactors including cascades of reaction vessels, loop reactors or flow tube reactors. More preferred are the efficient and advantageous preparations of nicotinamide and niacin, which serve as important members of the B-vitamin complex.

40 Claims, No Drawings

5,756,750

CONTINUOUS PROCESSES FOR THE HYDROLYSIS OF CYANOPYRIDINES UNDER SUBSTANTIALLY ADIABATIC CONDITIONS

BACKGROUND

This application claims priority of provisional application No. 60/011,424 filed on Feb. 9, 1996.

This invention relates to a continuous process for the hydrolysis of cyanopyridines, and in particular to such a process conducted under substantially adiabatic conditions. The hydrolysis conditions can be controlled to produce amides, carboxylic acids or their mixtures as major products.

Several products resulting from the hydrolyses of cyanopyridines are well-known products of commerce. For example, pyridine substituted amides and carboxylic acids are important vitamins, precursors to medicines and chemical intermediates. In the area of amides, the best known example includes niacinamide (also known as nicotinamide and 3-pyridine carboxamide) and in the area of carboxylic acids, the best know example includes niacin (also known as nicotinic acid and 3-pyridine carboxylic acid). Niacinamide and niacin, both commonly referred to as vitamin $B_3$, are members of the B-vitamin complex and precursors of coenzymes I and II, and are important supplements to the diet of humans and animals. Pellegra related deaths in the United States caused by vitamin $B_3$ deficiency dropped from 7,358 in 1929, to 70 in 1956, primarily as a result of increased availability of vitamin $B_3$. Higher growth rates occur in animals having diets supplemented with vitamin $B_3$ and in the case of ruminants, higher milk production also occurs. In 1985, the U.S. market for niacinamide and niacin was estimated at 6,700 metric tons. See Kirk-Othmer, *Encyclopedia of Chemical Technology*, Third Edition, Vol. 24, pages 59–93 for a general discussion of the $B_3$ Vitamins. Isonicotinic acid, a precursor to isonicotinic acid hydrazide (isoniazid) and related drugs used in the treatment of tuberculosis can be prepared by the hydrolysis of 4-cyanopyridine.

As to preparative methods for these compounds, cyanopyridines have frequently been hydrolyzed in batch and continuous processes with catalytic to stoichiometric excesses of a base. A majority of the methods reported have been batch processes. For example, 4-cyanopyridine in the presence of sodium hydroxide at a molar ratio of 1:(0.03–0.075) and at 120°–170° C. is reported to give isonicotinamide. See U.S.S.R. SU 1,553,531 (1990); CA:113:78174f (1990). Similarly, 2-cyanopyridine is reported to react with sodium hydroxide at a molar ratio of 1:(0.03–0.20) and at temperatures ranging from 100°–130° C. to give 2-picolinamide. See U.S.S.R. SU 1,553,530 (1990); CA:113:78173e (1990). With a molar ratio of 4-cyanopyridine:sodium hydroxide of 1:(1.5–1.75) and a hydrolysis temperature of 50°–80° C., the reported hydrolysis product was isonicotinic acid. See U.S.S.R. SU 1,288,183; CA:106:176187n (1987). The hydrolysis of 3-cyanopyridine with excess ammonia at 107°–109° C. for 12 hours was reported to give mixtures of nicotinamide and niacin. See J. Am Chem. Soc. 65, at pages 2256–7 (1943). In still another variation, the hydrolysis of 3-cyanopyridine has been reported with a polymeric base, Dowex 1X4 (in the hydroxide form), to yield nicotinamide. See Dutch Patent Application No. 7706612-A; CA:90:186814e. U.S. Pat. No. 4,314,064 describes the continuous hydrolysis of 3-cyanopyridine with 0.3 to 3.0 moles of an alkali metal hydroxide for each 100 moles of cyanopyridine at pressures of between 3 to 20 bars and with heating or cooling to maintain the prescribed reaction temperature. Similarly, 3-cyanopyridine is reported to react in a continuous process with aqueous ammonia at a molar ratio of 1:0.5 and a contact time of 40–50 minutes at 200°–260° C. to give nicotinamide. See Journal of Applied Chemistry of the USSR (English Translation: 45:2716–2718 (1972).

As an alternative to the hydration of cyanopyridines in the presence of bases, bacterial and enzymatic hydrolysis processes have been studied. U.S. Pat. No. 5,395,758, assigned to Sumitomo Chemical Company Ltd., describes the conversion of 2-, 3-, and 4-cyanopyridine into their corresponding amides using cultured broths of an Agrobacterium bacteria. Japanese Patent No. 9300770000, assigned to Nitto Chemical Ind. Co. Ltd., describes the hydration of aromatic nitrites, including 3- and 4-cyanopyridine, using the action of Corynebacterium or Nocardia bacterium to give the corresponding aromatic amides with high selectivities.

In view of this background there remains a need and demand for a continuous process for the hydrolysis of cyanopyridines which provides for increased production rates while also providing high yields and product selectivity. Additionally, the continuous process should be capable of being operated employing starting materials which are readily available, and in simple equipment requiring minimal controls. The present invention addresses these needs.

SUMMARY

A feature of the present invention is the discovery that the continuous hydrolysis of cyanopyridines can be carried out in the presence of a base and under substantially adiabatic conditions to provide a vigorous reaction which surprisingly leads to increased production rates with high yields and selectivities. Thus one preferred embodiment of the invention provides a continuous process for hydrolyzing a cyanopyridine (for example 2-, 3-, or 4-cyanopyridine) by combining two or more feed streams to form a reaction mixture containing the cyanopyridine, water, and a base (for example, ammonia, an alkali metal hydroxide or an alkali metal carbonate) and reacting the reaction mixture under substantially adiabatic conditions. Processes of the invention can be carried out in a variety of continuous systems including for example a simple flow tube, require no temperature control other than an initiation temperature and can be substantially completed in less than a minute. For a given cyanopyridine, the required initiation temperature is a function of the cyanopyridine's reactivity toward hydrolysis and its concentration in addition to the base utilized and the ratio of that base to the cyanopyridine. The ratio of base to cyanopyridine also affects whether the major product is an amide or a carboxylic acid. Preferred hydrolyses of 2-cyanopyridine, 3-cyanopyridine and 4-cyanopyridine can be controlled to produce picolinamide, picolinic acid, nicotinamide, niacin, isonicotinamide or isonicotinic acid at surprisingly high production rates, with unexpected selectivities and surprisingly short reaction times.

Another preferred embodiment of the present invention provides a process which includes the steps of combining a first stream containing a cyanopyridine with a second stream containing water and a base, where at least one of the streams is heated to a temperature of about 20° to about 300° C., and passing the streams after they are combined through a reaction zone, to cause the hydrolysis to proceed under substantially adiabatic conditions. The first stream can include only a cyanopyridine as a melt or can additionally include water and/or another non-interfering solvent.

Although several reactor designs including a series of cascade reactors, loop reactors, or flow tubes can provide a suitable reaction zone a flow tube reactor is preferred. Preferred hydrolysis reactions include the hydrolysis of 3-cyanopyridine with alkali metal hydroxides such as sodium or potassium hydroxide to give nicotinamide or niacin in high yields and conversions with a minimum of impurities.

DESCRIPTION

For the purposes of promoting an understanding of the principles of the invention, reference will now be made to certain of its embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, the present invention provides unique processes for the continuous hydrolyses of cyanopyridines in the presence of a base under substantially adiabatic conditions, which surprisingly lead to increased production rates with high yields and selectivities. In this regard, the term "substantially adiabatic conditions" is meant to include conditions wherein substantially all of the heat generated by the hydrolysis reaction is retained within the reaction mixture during the period of reacting. That is, substantially no effort is made to cool the combined reactants within the reaction zone during the period of reacting. As a result, heat from the hydrolysis reaction is usually generated faster than it can be dissipated to surrounding regions and the temperature of the reaction mixture within the reaction zone reaches substantially that temperature caused by the uncontrolled exotherm of the hydrolysis reaction. Typically, the temperature of the reaction mixture increases by at least about 20° C. "Reaction zone" is meant to include a region within a continuous reactor where a cyanopyridine combined with a base undergoes a rapid exothermic reaction producing the hydrolysis product. Applicant's preferred process can be carried out in a variety of continuous systems, only requires control of the flow rates and initiation temperature and is completed within less than about thirty seconds after initiation has occurred.

The continuous hydrolysis of cyanopyridines according to embodiments of the preferred process produces primarily amides, carboxylic acids or their mixtures. 2,- 3-, and 4-Cyanopyridines are hydrolyzed with the applicants' preferred process to give picolinamide, picolinic acid, nicotinamide, niacin, isonicotinamide and isonicotinic acid. In addition, a wide variety of substituted and unsubstituted cyanopyridines are also suitable for use in the invention. Representative substituents include groups such as alkyl having up to about 9 carbon atoms, aryl, cyano, amino, alkylamino, hydroxy, and halo (e.g. —Cl and —Br) etc. Suitable substituents may remain unchanged as a result of the hydrolysis reaction or may be transformed during hydrolysis into a new substituent. The preferred cyanopyridines for use in the hydrolysis process include non-substituted cyanopyridines (2-cyanopyridine, 3-cyanopyridine, and 4-cyanopyridine) and substituted cyanopyridines with up to four additional groups which do not detrimentally interfere with the hydrolysis reaction and are either commercially available or can be obtained by methods known to the art and literature. More preferred cyanopyridines are non-substituted 2-cyanopyridine, 3-cyanopyridine, and 4-cyanopyridine, for example as can be obtained from Reilly Industries, Inc., of Indianapolis, Ind. and the Cambrex Corporation, East Rutherford, N.J. Although not necessary for the present invention, it is preferred that the cyanopyridines used be of high purity, for example about 95 to about 99.9% or more pure.

A variety of bases are known to facilitate hydrolysis reactions and the particular base employed is not critical to the broad aspects of the invention. Suitable bases for use in the invention generally include those bases compatible with the aqueous hydrolysis system which accelerate the hydrolysis of cyanopyridines. Preferred bases for use in the invention are ammonia, alkali metal hydroxides such as sodium or potassium hydroxide and alkali metal carbonates such as sodium or potassium carbonate. Although not required, the bases are commonly used in solution, more preferably in water. Preferred aqueous solutions of base have contained from about 5 to about 50% by weight base.

Processes of the invention can be conducted with varying amounts of water relative to cyanopyridine so as to control the reaction product, to improve the products flow through the reactor, and to effect the magnitude of the temperature increase caused by the uncontrolled exothermic hydrolysis reaction. The preferred amount of water for control of reaction product depends on the number of cyano groups on the cyanopyridine undergoing hydrolysis and whether amide or carboxylic acid groups are desired. For hydration, each cyano group reacts with one (1) molecule of water to give an amide group and two (2) molecules of water to give a carboxylic acid group. As a result, the preferred number of moles of water per mole of cyanopyridine utilized for product control can be determined for each cyanopyridine by adding (a) the number of cyano groups being hydrolyzed to amide groups multiplied by one (1), and (b) the number of cyano groups being hydrolyzed to carboxylic acid groups multiplied by two (2). For preferred processes, at least a slight excess of water is typically used. It can be added separately, with the cyanopyridine, with the base or some combination thereof. Typically, water is added with both the cyanopyridine and the base for feed to processes of the invention. Preferred cyanopyridine solutions have been from about 20% to about 85% by weight cyanopyridine in water, with more preferred cyanopyridine solutions containing from about 35% to about 70% by weight cyanopyridine, for amide and for carboxylic acid formation.

In preferred processes, a cyanopyridine, at least one base, and sufficient water are combined in a continuous manner to give a reaction mixture at an initial temperature sufficient to initiate and maintain hydrolysis without additional heating and sufficient to cause the rapid hydrolysis of the cyanopyridine. This initial temperature is referred to herein as the initiation temperature. To initiate hydrolysis when heating is necessary, at least one reactant stream can be preheated to a temperature sufficient to cause the reaction mixture to reach the initiation temperature and begin hydrolysis immediately upon combining the reactant streams. The amount of heating necessary is a function of the quantities and heat capacities of the various streams being combined as well as the concentrations of the reactants. For aqueous cyanopyridine solutions ranging between about 20% to about 85% by weight cyanopyridine, initiation temperatures between about 20° to about 300° C. have proven sufficient. For amide formation, initiation temperatures of about 60° to about 140° C. have been most preferred while for carboxylic acid formation, initiation temperatures of about 60° to about 200° C. have been most preferred. In advantageous processes, the hydrolysis is rapid and exothermic, causing a rapid increase in the temperature of the combined reactant streams within the reaction zone. For example, in more advantageous processes, the hydrolysis reaction has caused the temperature of the reaction mixture to increase by at least about 20° C. and the reaction is completed within less than about 30 seconds and typically in less than about 5 seconds.

The choice of base and its amount relative to the cyanopyridine can be controlled to cause the product to contain primarily a preferred amide or a preferred carboxylic acid. With stronger bases such as sodium and potassium hydroxide smaller quantities of base are adequate, while with weaker bases such as ammonia, larger quantities of base are required. Control of these parameters to achieve the desired products or product mixtures will be well within the purview of one skilled in the art given the teachings herein. Because bases can be either monobasic or dibasic and cyanopyridines can have more than one cyano group, the relative amounts of these reactants can be effectively understood in terms of equivalents. The number of equivalents of base can be determined by multiplying the number of moles of a base (determined in the usual manner) by the number of protons a mole of that base will react with. The number of equivalents of cyanopyridine can be determined by multiplying the number of moles of a cyanopyridine (determined in the usual manner) by the number of cyano groups present. The ratio of base to cyanopyridine will be a ratio of the number of equivalents of base per equivalents of cyanopyridine. In the preferred process, the ratio of base to cyanopyridine can vary depending on the hydrolysis product desired, the strength of the base utilized and the amount of water present. Generally, amide formation is favored when the ratio of equivalents of base to equivalents of cyanopyridine is about (0.01 to 50):100 and acid formation is favored when the ratio of equivalents of base to equivalents of cyanopyridine is about (50 to 200):100.

Although the present continuous hydrolysis can be carried out in a variety of customary continuous processing apparatuses such as cascades of reaction vessels, loop reactors or flow tubes, a flow tube reactor is preferred. For the preferred process, at least two reactant streams together containing cyanopyridine, water, and base are fed into a reactor, with sufficient heat applied to at least one of the reactant streams to cause the combined streams to reach an initiation temperature. Although not required, the reactant streams can pass through a mixing region immediately prior to entering the reactor or as an initial stage of the reactor. The mixing region can include a static mixer, a region containing packing materials or other mechanical forms known in the art. The reactor can also be equipped to operate at ambient pressure or at a prescribed pressure above atmospheric pressure. Because of the uncontrolled exothermic nature of the hydrolysis, reactors designed to operate above atmospheric pressure have generally been equipped with a pressure relieve valve vented to a catch pot and set below the pressure limit of the reactor. After hydrolysis, the reaction products exit the reactor and can pass into a receiver for future processing or can pass directly into a recovery system.

For the preferred continuous processes high production rates, selectivities, and yields are typically obtained. For instance, for nicotinamide formation by hydrolysis of 3-cyanopyridine, production rates ranging from between about 200 to several thousand kg per hour per liter of reactor volume can be obtained, with the applicant's work in systems to date readily achieving about 200 to about 1000 kg per hour per liter and more often about 400 to about 900 kg per hour per liter. Similar production rates can be and have been obtained for the hydrolysis of 3-cyanopyridine to niacin. The yields of amides and carboxylic acids utilizing the preferred continuous process have typically ranged between about 95% to about 99.5% with usually between about 0 to about 0.2% of unreacted nitrile remaining. By-products, either amide or carboxylic acid, have typically ranged between about 1 to about 5%.

Products from the continuous hydrolysis can be isolated by conventional methods. These methods include known batch or continuous crystallization methods, batch or continuous evaporative procedures, or combinations thereof. Niacinamide suitable for feed grade applications can be obtained by continuously dehydrating or drying the hydrolysis mixture utilizing a falling film evaporator and cooling belt technology, for example as described in U.S. Pat. No. 4,314,064. Carboxylic acid products can be recovered by first reacting the basic salt with an acid and isolating the free carboxylic acid by conventional methods such as crystallization. The hydrolysis products obtained by the process of the present invention are useful as vitamins (i.e. niacinamide and niacin), as chemical intermediates in the manufacture, for example, of products used in the agricultural and pharmaceutical industries.

For the purposes of promoting a further understanding of the present invention and its preferred features and embodiments, the following examples are being provided. It will be understood, however, that these examples are illustrative, and not limiting, in nature.

Examples 1–10 were carried out in a 1 liter autoclave to simulate the first stage of a cascade of reaction vessels. Examples 11–14 were carried out in a flow tube reactor. Hydrolysis reactions to give pyridine substituted carboxylic acids have given similar results in both reactors. However, better selectivity for amide formation has been obtained in the flow tube reactor. For all examples the compositions of solutions are given in weight percents.

EXAMPLES 1–10

Examples 1–10 set forth in Table 1 were conducted using the following procedure. An aqueous solution of the indicated cyanopyridine (abbreviated "CN") was heated in a stirred stainless steel autoclave equipped with a heating mantle to an initiation temperature, heating was discontinued and an aqueous solution of the indicated base was quickly injected (typically in less than 5 seconds). When the temperature of the reaction mixture began to drop, the maximum temperature was noted, the heating mantle dropped and the autoclave was cooled rapidly in cold water. The reaction mixture was analyzed by HPLC to determine the amounts of the corresponding amide, carboxylic acid and cyanopyridine. As examples 1–10 demonstrate, the cyanopyridine concentrations, choice of base, amount of base, and the initiation temperature can be controlled in the hydrolysis of cyanopyridines under substantially adiabatic conditions to produce pyridine substituted amides and carboxylic acids. The choice of conditions produces high yields of the pyridine substituted amide or carboxylic acid.

TABLE 1

| Example No. | 1 | 2 | 3 | 4 | 5 | 6 | 7 | 8 | 9 | 10 |
|---|---|---|---|---|---|---|---|---|---|---|
| Cyanopyridine | 3-CN | 3-CN | 3-CN | 3-CN | 3-CN | 4-CN | 4-CN | 2-CN | 3-CN | 2-CN |
| concentration | 42.3% | 65.2% | 77.3% | 22.1% | 63.3% | 51.8% | 63.7% | 51.8% | 51.8% | 51.8 |
| amount, mL | 182 | 177 | 174 | 177 | 152 | 186 | 151 | 186 | 186 | 186 |
| Base | NaOH | NaOH | NaOH | NaOH | NaOH | $NH_3$ | $NH_3$ | $NH_3$ | $NH_3$ | $Na_2CO_3$ |
| concentration | 10% | 10% | 10% | 40% | 40% | 29% | 29% | 29% | 29% | 15% |
| amount, mL | 12 | 18 | 21 | 28 | 70 | 10 | 60 | 10 | 10 | 11 |
| Initial Temperature | 125° C. | 115° C. | 105° C. | 200° C. | 200° C. | 115° C. | 200° C. | 115° C. | 115° C. | 115° C. |
| Maximum Temperature | 147° C. | 152° C. | 155° C. | 205° C. | 216° C. | 116° C. | 200° C. | 117° C. | 115° C. | 128° C. |
| Ratio of Base:Cyanopyridine | 14.3:100 | 14.3:100 | 14.3:100 | 104:100 | 104:100 | 15.9:100 | 95.2:100 | 15.9:100 | 15.9:100 | 0.9:100 |
| Products | | | | | | | | | | |
| amide | 94.2% | 94.8% | 95.1% | 1.7% | 8.0% | 25.4% | 45.1% | 0.5% | 2.9% | 73.1% |
| cyanopyridine | 0.2% | 0.0% | 0.2% | 0.0% | 0.0% | 73.2% | 51.8% | 99.4% | 97.1% | 26.1% |
| carboxylic acid | 5.6% | 5.2% | 4.7% | 98.3% | 92.0% | 1.3% | 3.1% | 0.1% | 0.0% | 0.8% |

EXAMPLES 11–14

The continuous hydrolysis of 3-cyanopyridine was carried out in an insulated flow tube reactor having a length of 5.5 feet and an inner diameter of 1.049 inches and no means for cooling. At one end, the reactor was connected in series to a static mixer, a heater, and a pump for introducing the 3-cyanopyridine solution. Between the static mixer and the pump, was an inlet pipe for introducing an aqueous solution of sodium hydroxide. Thermocouples were placed: (a) between the heater and the static mixer, (b) at the entry of the reactor and (c) near the exit of the reactor. At its exit, the reactor was connected to a receiver equipped with a water condenser. Between the reactor and the receiver were placed (a) nearer the reactor, a pressure relief valve and (b) nearer the receiver a back pressure regulator set at approximately 200 psi or alternatively, a ball valve restricted to create the desired pressure.

For Example 11, an aqueous solution containing 60% by weight of 3-cyanopyridine was fed through the heater at a uniform rate of 142 gallons/hour, increasing its temperature to 115° C. A 7% aqueous solution of sodium hydroxide was metered into the 3-cyanopyridine stream at a uniform rate of 5 gallons/hour and the combined streams fed into the reactor through the static mixer. The combined reactants entered the flow tube reactor at a temperature of 116° C., reached a temperature of 156.9° C. within about 4 seconds and immediately exited the reactor and passed into the holding vessel. The ratio of sodium hydroxide to cyanopyridine was 1.1:100. A sample of the hydrolysis product was analyzed and found to contain on a water free basis: a) 96.04% nicotinamide; b) 0.23% 3-cyanopyridine; and c) 3.73% sodium nicotinate. Table 2 summarizes the results from Examples 11–14 carried out in a flow tube reactor utilizing the method described above. Other substituted cyanopyridines, including 2-cyanopyridine and 4-cyanopyridine, can be hydrolyzed in the flow tube reactors to give amides, carboxylic acids, or mixtures. For the hydrolysis of 2-cyanopyridine or its derivatives to give the carboxylic acid, maximum temperatures above about 135° C. should be avoided to prevent decarboxylation of the initially formed carboxylic acid.

TABLE 2

| Example No. | 11 | 12 | 13 | 14 |
|---|---|---|---|---|
| 3-Cyanopyridine | | | | |
| concentration | 60% | 60% | 60% | 60% |
| flow-rate, gal/hr | 142 | 161 | 140 | 145.6 |
| Sodium Hydroxide | | | | |
| concentration | 7% | 6.6% | 6.6% | 8.1% |
| flow-rate, gal/hr | 5 | 2.2 | 10.8 | 6.64 |
| Initiation Temperature, °C. | 115 | 120 | 115 | 110 |
| Maximum Temperature, °C. | 156.9 | 190 | 195.8 | >200 |
| NaOH:Cyanopyridine Product | 1.1:100 | 0.4:100 | 2.3:100 | 1.7:100 |
| nicotinamide, % | 96.04 | 93.17 | 96.04 | 96.99 |
| cyanopyridine, & | 0.23 | 5.66 | 0.00 | 0.00 |
| sodium nicotinate, % | 3.73 | 1.16 | 3.96 | 3.01 |

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

All publications cited herein are indicative of the level of skill in the art and are hereby incorporated by reference as if each had been individually incorporated by reference and fully set forth.

What is claimed is:

1. A continuous process for the hydrolysis of a cyanopyridine, comprising continuously combining two or more feed streams to provide a reaction mixture including a cyanopyridine, water, and a base, and reacting the reaction mixture under substantially adiabatic conditions.

2. The process of claim 1, wherein the cyanopyridine is selected from the group consisting of 2-cyanopyridine, 3-cyanopyridine, and 4-cyanopyridine.

3. The process of claim 2, wherein said reacting is initiated at a temperature of at least about 20° C., and wherein said base is present in an amount less than 50 equivalents of base per 100 equivalents of cyanopyridine.

4. The process of claim 3, which includes reacting about 0.01 to about 10 equivalents of base per 100 equivalents of the cyanopyridine and said reacting is initiated at a temperature of about 60° to about 140° C. to and forms a product comprising a pyridine substituted amide.

5. The process of claim 4, wherein said base is ammonia.

6. The process of claim 5, wherein said cyanopyridine is 3-cyanopyridine and said pyridine substituted amide is niacinamide.

7. The process of claim 4, wherein said base is an alkali metal hydroxide.

8. The process of claim 7, wherein the cyanopyridine is 3-cyanopyridine, the alkali metal hydroxide is sodium or potassium hydroxide and the product comprises niacinamide.

9. The process of claim 4, wherein the base is an alkali metal carbonate.

10. The process of claim 9, wherein the cyanopyridine is 3-cyanopyridine, the alkali metal carbonate is sodium or potassium carbonate and the product comprises niacinamide.

11. The process of claim 10, wherein said process includes recovering niacinamide.

12. The process of claim 1, wherein the cyanopyridine is selected from the group consisting of 2-cyanopyridine, 3-cyanopyridine, and 4-cyanopyridine.

13. The process of claim 12, wherein said reacting is initiated at a temperature of at least about 20° C., and wherein said base is present in an amount of at least 50 equivalents of base per 100 equivalents of cyanopyridine.

14. The process of claim 13, which includes reacting about 50 to about 200 equivalents of base per 100 equivalents of the cyanopyridine, and wherein said reacting is initiated at a temperature of about 60° to about 200° C. and forms a product comprising a pyridine substituted carboxylic acid.

15. The process of claim 14, wherein the base is ammonia.

16. The process of claim 15, wherein the cyanopyridine is 3-cyanopyridine and the product comprises niacin.

17. The process of claim 14, wherein the base is an alkali metal hydroxide.

18. The process of claim 17, wherein the cyanopyridine is 3-cyanopyridine, the alkali metal hydroxide is sodium or potassium hydroxide and the product comprises niacin.

19. The process of claim 14, wherein the base is an alkali metal carbonate.

20. The process of claim 19, wherein the cyanopyridine is 3-cyanopyridine, the alkali metal carbonate is sodium or potassium carbonate and the product comprises niacin.

21. A continuous process for the hydrolysis of a cyanopyridine, comprising the steps of:

combining a first stream containing said cyanopyridine with a second stream containing water and a base, wherein at least one of the streams is heated to a temperature of about 20° to about 300° C.; and passing the streams after said combining through a reaction zone and causing a hydrolysis reaction to proceed under substantially adiabatic conditions.

22. The process in claim 21, wherein the first stream contains about 20 to about 85% by weight cyanopyridine and the second stream contains about 5 to about 50% by weight of said base.

23. The process in claim 22, which includes reacting about 0.01 to about 10 equivalents of base per 100 equivalents cyanopyridine, said reacting being initiated at a temperature of about 60° to about 140° C. and forming a product comprising a substituted amide.

24. The process in claim 23, wherein the cyanopyridine is 3-cyanopyridine, the base is sodium or potassium hydroxide and the product comprises niacinamide.

25. The process of claim 22, which includes reacting at least 50 equivalents of base per 100 equivalents of cyanopyridine, said reacting being initiated at a temperature of about 60° to about 200° C. and forming a product comprising a substituted carboxylic acid.

26. The process of claim 25, wherein the cyanopyridine is 3-cyanopyridine, the base is sodium or potassium hydroxide and the product comprises niacin.

27. The process of claim 21, wherein said first stream contains 3-cyanopyridine and said hydrolysis reaction is conducted in a flow tube reactor.

28. The process of claim 27, wherein said first stream contains from about 20% to about 85% by weight 3-cyanopyridine.

29. The process of claim 28, wherein the base is selected from a group consisting of ammonia, sodium hydroxide, sodium carbonate, potassium hydroxide, and potassium carbonate.

30. The process of claim 29, wherein the hydrolysis reaction is initiated at a temperature of about 20° to about 300° C. and the base is sodium or potassium hydroxide.

31. The process of claim 30, wherein said base is present in an amount less than about 50 equivalents of base per 100 equivalents of 3-cyanopyridine, the hydrolysis reaction is initiated at a temperature of about 60° to about 140° C. and forms a product comprising niacinamide.

32. The process of claim 30, wherein the base is present in an amount of at least 50 equivalents of base per 100 equivalents of 3-cyanopyridine, the hydrolysis reaction is initiated at a temperature of about 60° to about 200° C. and forms a product comprising niacin.

33. A continuous process for the hydrolysis of a cyanopyridine, comprising continuously reacting a reaction mixture including cyanopyridine, water and a base, wherein said reacting is initiated at a temperature of at least 20° C. and produces an increase in the temperature of said reaction mixture of at least 20° C.

34. The process of claim 33, wherein the cyanopyridine is 3-cyanopyridine and said process includes reacting about 0.01 to about 10 equivalents of base per 100 equivalents of 3-cyanopyridine and forms a product comprising niacinamide.

35. The process of claim 34, wherein said base is selected from the group consisting of ammonia, sodium hydroxide, sodium carbonate, potassium hydroxide and potassium carbonate.

36. The process of claim 35, wherein the cyanopyridine is 3-cyanopyridine and said process includes reacting at least 50 equivalents of base per 100 equivalents of 3-cyanopyridine and the product comprises niacin.

37. The process of claim 36, wherein said base is selected from the group consisting of ammonia, sodium hydroxide, sodium carbonate, potassium hydroxide and potassium carbonate.

38. The process of claim 33, wherein said reacting is substantially complete in less than about 30 seconds, and in that 30 seconds produces an increase in the temperature of said reaction mixture of at least about 20° C.

39. The process of claim 33, wherein substantially all heat generated by said reacting is retained within the reaction mixture during said reacting.

40. A continuous process for the hydrolysis of a cyanopyridine, comprising the steps of:

continuously forming and passing through a reaction zone, a reaction mixture including the cyanopyridine, water and a base;

initiating an exothermic hydrolysis reaction of the reaction mixture in the reaction zone; and retaining in said reaction mixture during said hydrolysis reaction, substantially all heat generated by said hydrolysis reaction.

\* \* \* \* \*

UNITED STATES PATENT AND TRADEMARK OFFICE
CERTIFICATE OF CORRECTION

PATENT NO. : 5,756,750
DATED : May 26, 1998
INVENTOR(S) : Wei Cao et al.

It is certified that error appears in the above-identified patent and that said Letters Patent is hereby corrected as shown below:

In col. 2, line 16, please delete "nitrites" and insert in lieu thereof --nitriles--.

In cols. 7-8, Table 1, the second line of the table under column 10 of the table, please delete "51.8" and insert in lieu thereof --51.8%--.

Signed and Sealed this

Twenty-fifth Day of May, 1999

Attest:

Q. TODD DICKINSON

Attesting Officer

Acting Commissioner of Patents and Trademarks